(12) United States Patent
Schweinsberg et al.

(10) Patent No.: US 8,814,952 B2
(45) Date of Patent: Aug. 26, 2014

(54) GENTLE HAIR DYE

(71) Applicant: Henkel AG & Co. KGaA, Duesseldorf (DE)

(72) Inventors: Matthias Schweinsberg, Hamburg (DE); Jisook Baek, Hamburg (DE); Astrid Kleen, Hamburg (DE); Erik Schulze zur Wiesche, Hamburg (DE); Antje Gebert, Duesseldorf (DE); Monika Nebel, Norderstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/132,131

(22) Filed: Dec. 18, 2013

(65) Prior Publication Data

US 2014/0165302 A1     Jun. 19, 2014

(30) Foreign Application Priority Data

Dec. 19, 2012   (DE) .......................... 10 2012 223 805

(51) Int. Cl.
  *A61Q 5/10*      (2006.01)
  *A61K 8/25*      (2006.01)
  *A61K 8/58*      (2006.01)
  *A61K 8/898*     (2006.01)

(52) U.S. Cl.
  CPC ... *A61Q 5/10* (2013.01); *A61K 8/25* (2013.01); *A61K 8/585* (2013.01); *A61K 8/898* (2013.01)
  USPC ............................ 8/405; 8/406; 8/407; 8/581

(58) Field of Classification Search
  CPC .......... A61Q 5/10; A61K 8/25; A61K 8/585; A61K 8/898
  USPC ....................................... 8/405, 406, 407, 581
  See application file for complete search history.

(56) References Cited

U.S. PATENT DOCUMENTS

| | | | |
|---|---|---|---|
| 6,824,764 B2 * | 11/2004 | Devin-Baudoin et al. | ... 424/70.1 |
| 7,220,408 B2 | 5/2007 | Decoster et al. | |
| 7,223,385 B2 | 5/2007 | Gawtrey et al. | |
| 7,485,289 B2 | 2/2009 | Gawtrey et al. | |
| 7,504,094 B2 | 3/2009 | Decoster et al. | |

FOREIGN PATENT DOCUMENTS

AU    2005256329 B2    1/2006

OTHER PUBLICATIONS

STIC Search Report dated Feb. 7, 2014.*

* cited by examiner

*Primary Examiner* — Eisa Elhilo
(74) *Attorney, Agent, or Firm* — David K. Benson

(57) ABSTRACT

The subject matter of the present invention is a method for oxidative coloring of keratinic fibers, in particular hair, in which a) a pretreatment agent that contains at least one 4-morpholinomethyl-substituted silicone of formula (V) is applied onto the keratinic fibers, in particular onto the hair, b) subsequently, within a time span of from about one second to about 24 hours after step a), a hair coloring agent is applied onto the keratinic fibers, which agent contains at least one oxidation dye precursor of the developer type and at least one oxidation dye precursor of the coupler type, as well as at least one oxidizing agent.

11 Claims, No Drawings

GENTLE HAIR DYE

CROSS-REFERENCE TO RELATED APPLICATIONS

This Application claims priority to German Patent Application DE 10 2012 223 805.0, filed Dec. 19, 2012, the contents of which are incorporated herein by reference in their entirety.

TECHNICAL FIELD

The present invention relates to a low-impact method for oxidative hair coloring in which keratinic fibers are protected from oxidizing influences.

BACKGROUND

In the context of oxidative hair coloring of hair, the problem arises that irritation of the scalp and damage to the keratinic fibers can occur as a result of the aggressive agents. In particular, the natural hydrophobicity of the keratinic fibers is reduced because the coloring agents resp. lightening agents must first make the hair capable of penetration in order to exert their effect. The water-repellent effect on the one hand, however, provides natural protection for the hair; on the other hand, parameters desired by the consumer, such as shine, softness, suppleness, and the "drape" of the hair, are closely linked to it.

In order to overcome the aforesaid disadvantages, so-called pretreatment agents that are intended to protect the hair from aggressive influences are on the market. These often make the hair heavy, however, or negatively affect the outcome of the lightening resp. coloring of the hair that takes place subsequently; in particular, the washing fastness of the color can be degraded by the pretreatment agent.

The object of the present invention is to make available a method for oxidative hair coloring, with a hair-protecting pretreatment, that overcomes the aforesaid disadvantages without counteracting the success of a subsequent oxidative coloring treatment. The intention is in particular to make available a method in which the hair is not made heavier, and in which the desired effect can also be achieved in the context of a pretreatment not occurring immediately before the oxidative coloring treatment, with the result that the time span between pretreatment and coloring can be extended.

The use of aminated silicones in hair care is established art. They are widely used in shampoos and in particular in conditioners in order to exert care-providing effects therein. EP 1771144 B1, for example, discloses hair-conditioning agents having aminofunctional silicones. The agents described therein are post-treatment agents.

European patents EP 1312334 B1 (aminosilicone and thickener) and EP 1312335 B1 (aminosilicone and conditioner) also disclose hair post-treatment agents. Extremely water-rich formulations are also disclosed in the former document.

BRIEF SUMMARY

Methods of oxidative coloring of keratinic fibers are provided. In an embodiment, a method is provided for oxidative coloring of keratinic fibers, in particular human hair, wherein
b. a pretreatment agent that comprises at least one 4-morpholinomethyl-substituted silicone of formula (V),

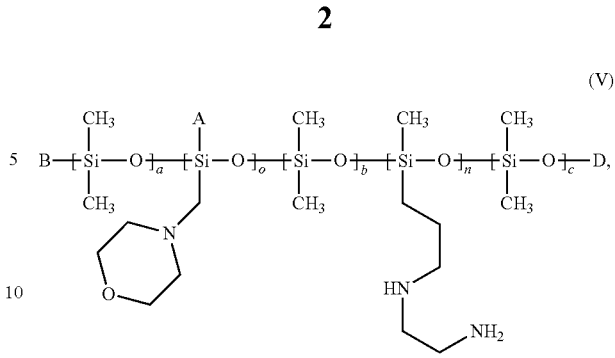

in which
A denotes a structural unit (I), (II), or (III) bound via —O—

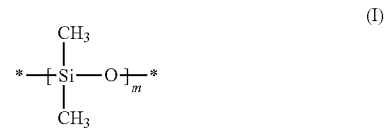

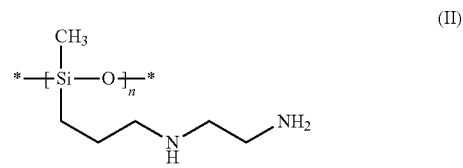

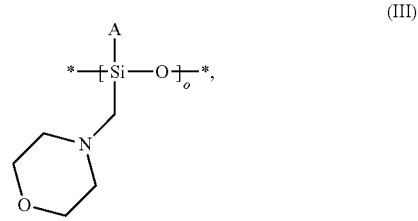

or an oligomeric or polymeric residue bound via —O— containing structural units of formulas (I), (II), or (III), or half of an oxygen atom connecting to a structural unit (III), or denotes —H,
* denotes a bond to one of the structural units (I), (II), or (III), or denotes a terminal group B (Si-bound) or D (O-bound),
B denotes an —OH, —O—Si(CH$_3$)$_3$, —O—Si (CH$_3$)$_2$OH, —O—Si(CH$_3$)$_2$OCH$_3$ group,
D denotes an —H, —Si(CH$_3$)$_3$, —Si(CH$_3$)$_2$OH, —Si (CH$_3$)$_2$OCH$_3$ group,
a, b, and c denote integers from about 0 to about 990, with the provision that a+b+c>0,
m, n, and o denote integers from about 1 to about 990,
is applied onto the keratinic fibers, in particular onto the hair.
c. subsequently, within a time span of from about one second to about 24 hours after step a), a hair coloring agent is applied onto the keratinic fibers, which agent comprises at least one oxidation dye precursor of the developer type and at least one oxidation dye precursor of the coupler type, as well as at least one oxidizing agent.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

It has now been found that a pretreatment of the keratinic fibers with special 4-morpholinomethyl-substituted silicones within a specific time period prior to an oxidative coloring treatment results not only in appreciably improved hair protection with no negative effect on the results of the oxidative coloring treatment, but also in particularly good coloring results, in particular colors having a high level of washing fastness. "Hair protection" is to be understood for purposes of the Application in particular to mean that the structure of the keratinic fibers, in particular of the hair, is less intensely attacked by the oxidizing agent, so that the surface of the fibers resp. of the hair becomes less roughened, the hair ends experience less splitting, and/or less hair breakage occurs.

The subject matter of the present invention is, in a first embodiment, a method for oxidative coloring of keratinic fibers, in particular human hair, in which a) a pretreatment agent that contains at least one 4-morpholinomethyl-substituted silicone of formula (V),

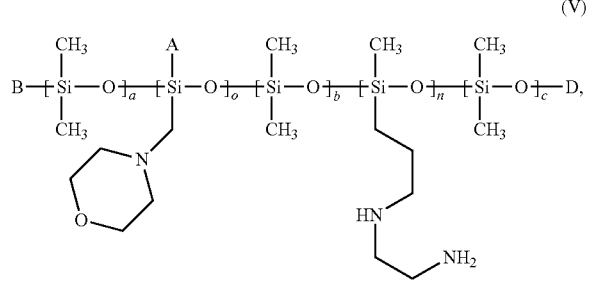

in which

A denotes a structural unit (I), (II), or (III) bound via —O—

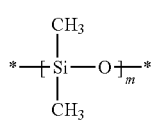

or an oligomeric or polymeric residue bound via —O— containing structural units of formulas (I), (II), or (III), or half of an oxygen atom connecting to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from about 0 to about 990, with the provision that a+b+c>0, m, n, and o denote integers from about 2 to about 990 is applied onto the keratinic fibers, in particular onto the hair, b) subsequently, within a time span from about one second to about 24 hours after step a), a hair coloring agent is applied onto the keratinic fibers, which agent contains at least one oxidation dye precursor of the developer type and at least one oxidation dye precursor of the coupler type, as well as at least one oxidizing agent.

Pretreatment agents preferably used according to the present invention are characterized in that they contain the at least one 4-morpholinomethyl-substituted silicone of formula (V), which comprises respectively at least one of the structural units of formulas (I), (II), and (III), in a total quantity of from about 0.001 to about 5 wt %, preferably about 0.005 to about 2 wt %, particularly preferably about 0.01 to about 1 wt %, extraordinarily preferably about 0.02 to about 0.1 wt %, based in each case on the total weight of the pretreatment agent.

Pretreatment agents preferably used according to the present invention are characterized in that they contain the at least one 4-morpholinomethyl-substituted silicone of formula (V) in a form emulsified in water. Pretreatment agents used particularly preferably contain about 30 to about 98 wt %, preferably about 40 to about 90 wt %, particularly preferably about 50 to about 85 wt %, extraordinarily preferably about 60 to about 80 wt % water, based in each case on the total weight of the pretreatment agent.

Pretreatment agents used particularly preferably are present in the form of an oil-in-water emulsion in which the number-average size of the silicone particles in the emulsion is in the range of from about 3 to about 500 nm, preferably in the range of from about 5 to about 60 nm.

Structural units of formulas (I), (II), and (III) can be present statistically distributed in the molecule, but the silicones used according to the present invention can also be block copolymers made up of blocks of the individual structural units, in which context the blocks can in turn be present in statistically distributed fashion.

The * on the free valences of structural units (I), (II), or (III) denotes a bond to one of the structural units (I), (II), or (III) or a terminal group B (Si-bound) or D (O-ound).

The silicones used according to the present invention can be trimethylsilyl-terminated at both ends (D=—Si(CH₃)₃, B=-O—Si(CH₃)₃), but they can also be dimethylsilylhydroxy- or dimethylsilylmethoxy-terminated at one or two ends. Silicones used particularly preferably in the context of the present invention have at least one terminal dimethylsilylhydroxy group, i.e. are selected from silicones in which B=—O—Si(CH₃)₂OH and D=—Si(CH₃)₃
B=—O—Si(CH₃)₂OH and D=—Si(CH₃)₂OH
B=—O—Si(CH₃)₂OH and D=—Si(CH₃)₂OCH₃
B=—O—Si(CH₃)₃ and D=—Si(CH₃)₂OH
B=—O—Si(CH₃)₂OCH₃ and D=—Si(CH₃)₂OH.

These silicones result in exorbitant improvements in the hair properties of the hair treated in accordance with the method according to the present invention, in particular in a tremendous decrease in contact angle.

In structural unit (III), residue A can denote
a structural unit (I), (II), or (III) bound via —O—, or
an oligomeric or polymeric residue bound via —O— containing structural units of formulas (I), (II), and (III), or
half of an oxygen atom connecting to a structural unit (III), or can denote —OH.

In the first case, structural unit (III) becomes one of the structural units (IIIa), (IIIb), or (IIIc):

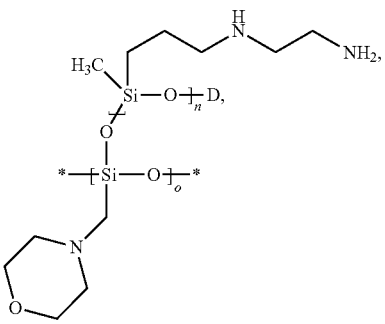
(IIIb)

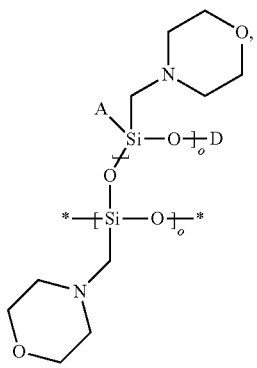
(IIIc)

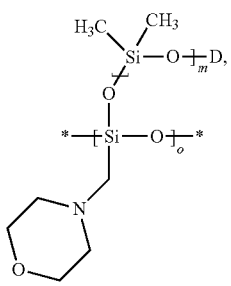
(IIIa)

where m=n=o=1, and A resp. D are as defined above.

In the second case, in the formulas (IIIa), (IIIb), and (IIIc) recited above the indices m, n, and o can denote integers of from about 2 to about 990. The second case also, however, covers oligomeric or polymeric residues that contain at least two different structural units of formulas (I), (II), or (III), as depicted in formula (IIId):

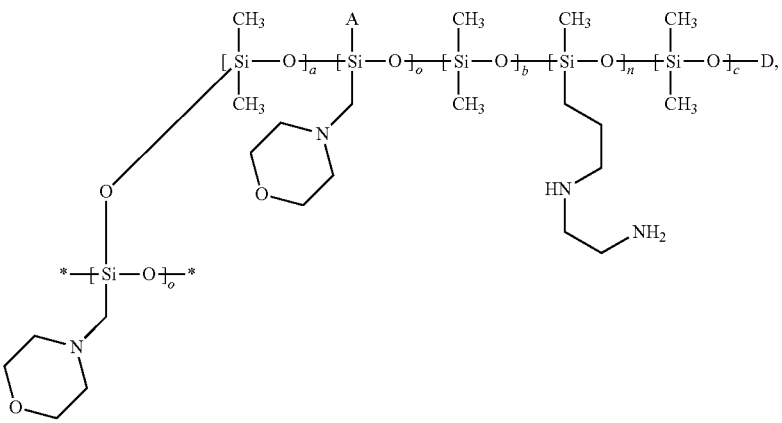
(IIId)

in which a, b, and c denote integers of from about 0 to about 990, with the provision that a+b+c>0, and n and o denote integers from about 1 to about 990.

In the third case, A denotes half of an oxygen atom connecting to a structural unit (III) (depicted in structural unit (IIIe)) or denotes —OH (depicted in structural unit (IIIf))

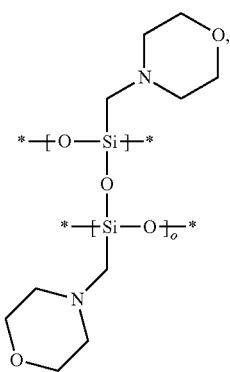

(IIIe)

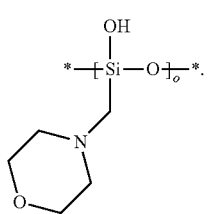

(IIIf)

As already mentioned, the structural units of formulas (I), (II), and (III) can by preference be present in statistically distributed fashion. Pretreatment agents preferably used according to the present invention contain at least one 4-morpholinomethyl-substituted silicone of formula (V)

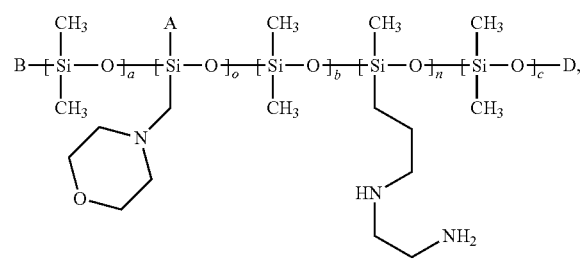

(V)

in which
A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from about 0 to about 990, with the provision that a+b+c>0, n, and o denote integers from about 1 to about 990.

Structural formula (V) is intended to illustrate the fact that the siloxane groups n and o do not obligatorily need to be bound directly to an end grouping B resp. D. Instead, in preferred formulas (V) a>0 or b>0, and in particularly preferred formulas (V) a>0 and b>0, i.e. the terminal grouping B resp. D is by preference bound to a dimethylsiloxy group. In formula (V) as well, the siloxane units a, b, c, n, and o are by preference statistically distributed.

The silicones represented by formula (V) and used according to the present invention can also be trimethylsilyl-terminated at both ends (D=—Si(CH$_3$)$_3$, B=—O-i(CH$_3$)$_3$), but they can also be dimethylsilylhydroxy- or dimethylsilylmethoxy-terminated at one or two ends. Silicones used particularly preferably in the context of the present invention have at least one terminal dimethylsilylhydroxy group, i.e. are selected from silicones in which B=—O—Si(CH$_3$)$_2$OH and D=—Si(CH$_3$)$_3$ B=—O—Si(CH$_3$)$_2$OH and D=—Si(CH$_3$)$_2$OH B=—O—Si(CH$_3$)$_2$OH and D=—Si(CH$_3$)$_2$OCH$_3$ B=—O—Si(CH$_3$)$_3$ and D=—Si(CH$_3$)$_2$OH B=—O—Si(CH$_3$)$_2$OCH$_3$ and D=—Si(CH$_3$)$_2$OH.

These 4-morpholinomethyl-substituted silicones of formula (V), which respectively comprise at least one of the structural units of formula (I), (II), and (III), sprisingly large improvements in the hair properties of the hair treated in accordance with the method according to the present invention, in particular in tremendously improved hair protection and color protection in the context of oxidative hair coloring.

In formula (V) as well, residue A can denote
a structural unit (I), (II), or (III) bound via —O—, or
an oligomeric or polymeric residue bound via —O— containing structural units of formulas (I), (II), and (III), or
half of an oxygen atom connecting to a structural unit (III), or can denote —OH.

By analogy with the statements regarding structural unit (III), formula (V) is thus refined to one of formulas (Va), (Vb), (Vc), (Vd,), (Ve), or (Vf):

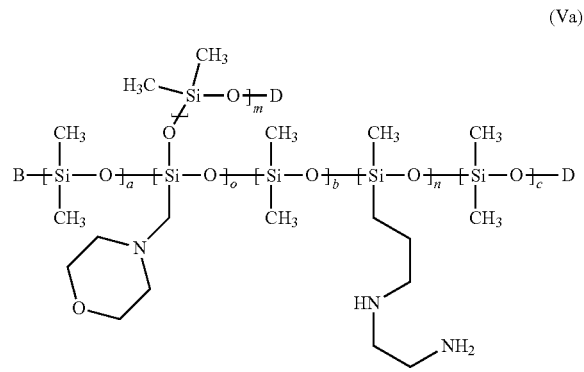

(Va)

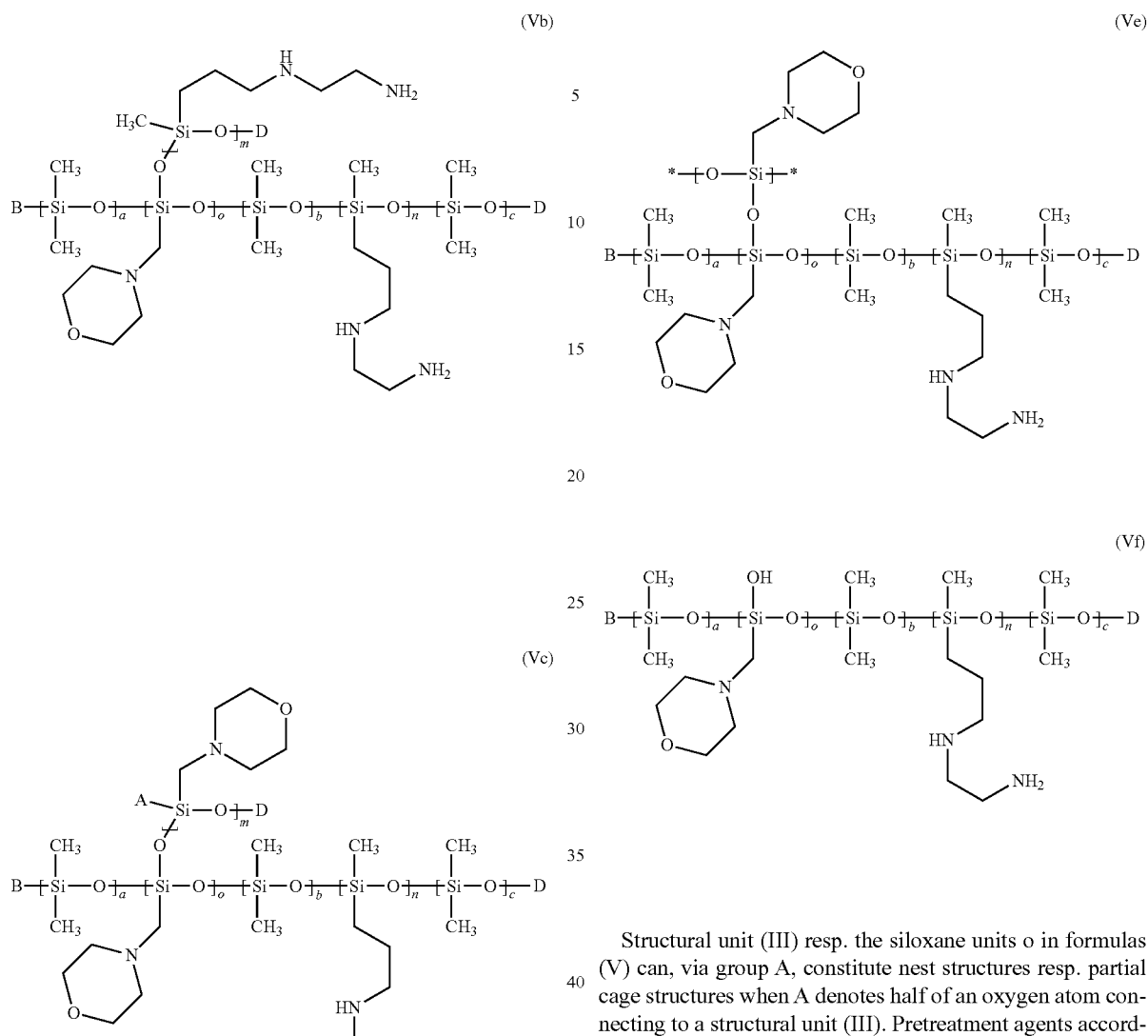

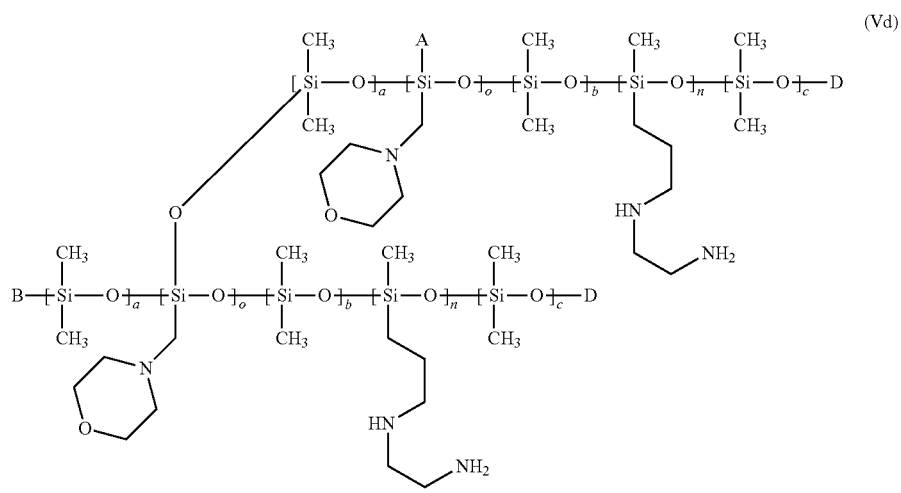

Structural unit (III) resp. the siloxane units o in formulas (V) can, via group A, constitute nest structures resp. partial cage structures when A denotes half of an oxygen atom connecting to a structural unit (III). Pretreatment agents according to the present invention that contain silicones having corresponding 4-morpholinomethyl-substituted silsesquioxane substructures are preferred according to the present invention, since these silicones result in enormously improved hair protection in the context of oxidative coloring treatment.

Pretreatment agents preferably used according to the present invention are characterized in that they contain at least one 4-morpholinomethyl-substituted silicone that comprises structural units of formula (VI)

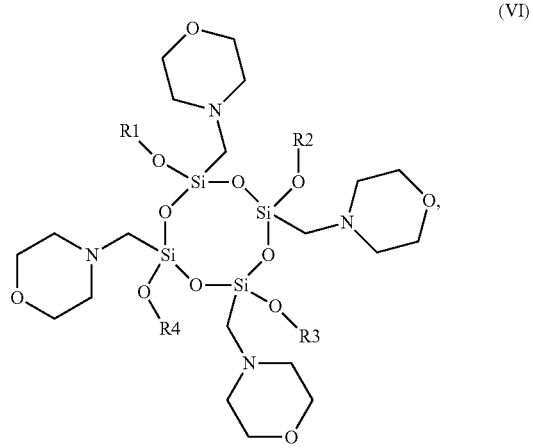

(VI)

in which

R1, R2, R3, and R4 mutually independently denote —H, —CH$_3$, a group D, a structural unit (I), (II), or (III), or an oligomeric or polymeric residue containing structural units of formulas (I), (II), or (III), or two of the residues R1, R2, R3, and R4 denote a structural unit —Si(R6)(R5)-, where R5=—CH$_3$ or a structural unit of formula (I) or (II) or (III) or an oligomeric or polymeric residue containing structural units of formulas (I), (II), or (III), R6=—OH, —CH$_3$, or a structural unit of formula (I) or (II) or (III) or an oligomeric or polymeric residue containing structural units of formulas (I), (II), or (III).

In preferred silicones of formula (VI), at least one of the residues R1, R2, R3, or R4 denotes an oligomeric or polymeric residue containing structural units of formulas (I), (II), or (III).

In further preferred silicones of formula (VI), at least one of the residues R1, R2, R3, or R4 denotes an oligomeric or polymeric residue containing structural units of formulas (I) and (II).

In even further preferred silicones of formula (VI), at least one of the residues R1, R2, R3, or R4 denotes an oligomeric or polymeric residue containing structural units of formulas (I) and (II) and (III).

At least one of the residues R1, R2, R3, or R4 by preference denotes an —[—Si(CH$_3$)$_2$—O]$_m$ grouping, i.e. an oligomer resp. polymer of structural unit (I). In addition, by preference structural unit (II) resp. an oligomer or polymer thereof is never bound in the molecule alone, but instead always in a statistical distribution with further structural units of formula (I) as one of the residues R1, R2, R3, or R4.

Preferred silicones of formula (VI) can be described by formula (VI a)

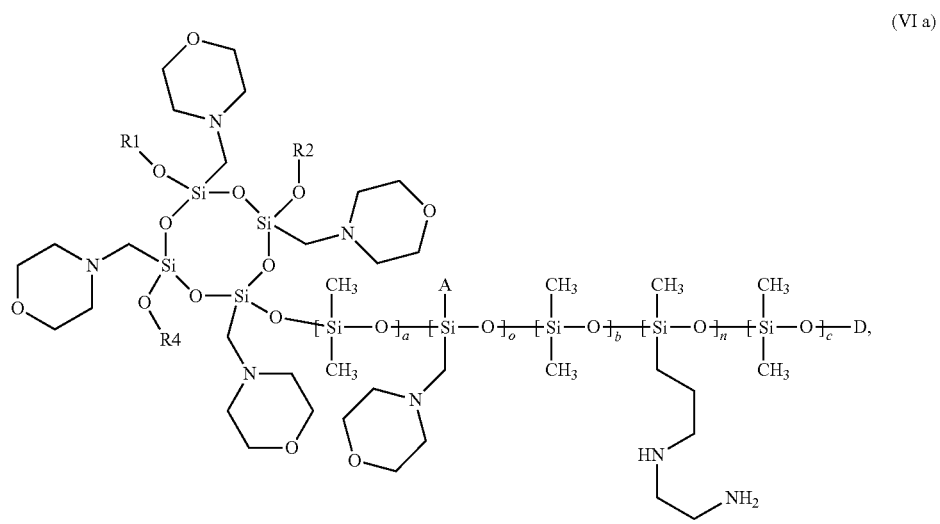

(VI a)

in which

R1, R2, and R4 mutually independently denote —H, —CH$_3$, a group D, a structural unit (I), (II), or (III), or an oligomeric or polymeric residue containing structural units of formulas (I), (II), or (III), or two of the residues R1, R2, and R4 denote a structural unit —Si(R6)(R5)-, where R5=—CH$_3$ or a structural unit of formula (I) or (II) or (III) or an oligomeric or polymeric residue containing structural units of formulas (I), (II), or (III), R6=—OH, —CH$_3$, or a structural unit of formula (I) or (II) or (III) or an oligomeric or polymeric residue containing structural units of formulas (I), (II), or (III), A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, a, b, and c denote integers from about 0 and about 990, with the provision that a+b+c>0, n, and o denote integers from about 1 and about 990.

Further preferred silicones of formula (VI) can be described by formula (VI b)

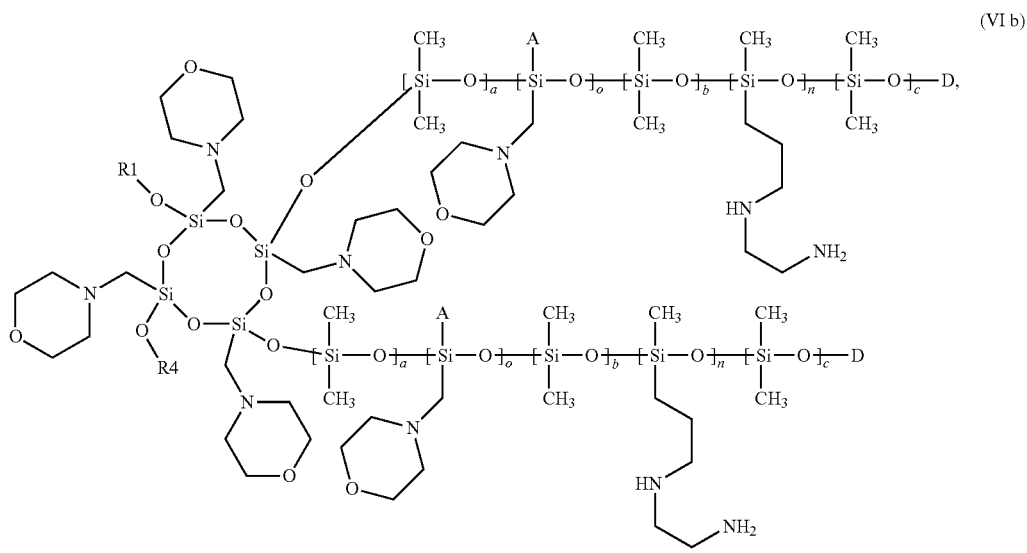

(VI b)

in which the residues and indices are as defined above.

Particularly preferred silicones of formula (VI) can be described by formula (VI c)

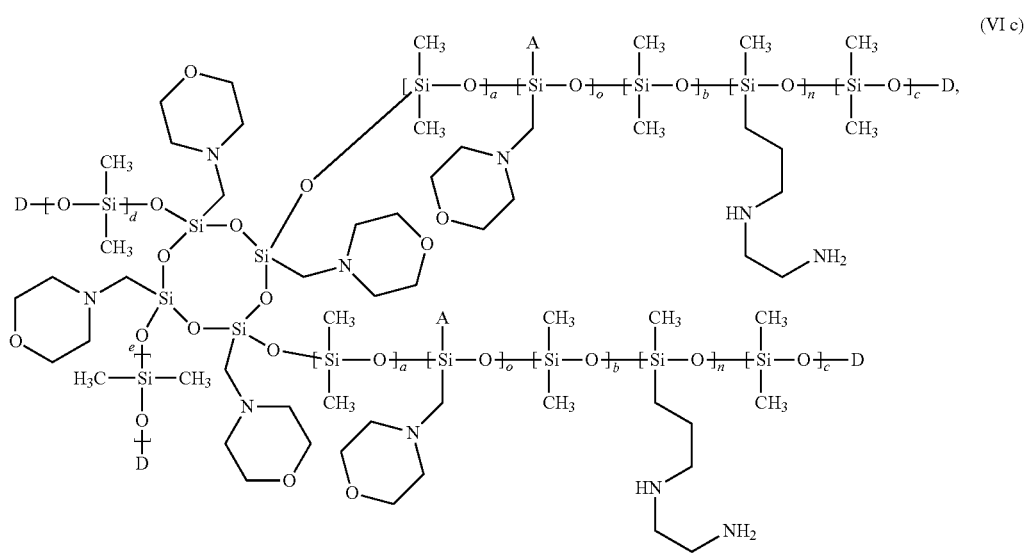

(VI c)

in which the residues and indices are as defined above, and the indices d and e denote integers from about 0 to about 990.

In formulas (VI a), (VI b), and (VI c), at least one of the groupings D by preference denotes —Si(CH₃)₂OH.

The silsesquioxane structures can be even more pronounced in the 4-morpholinomethyl-substituted silicones used according to the present invention, which intensifies the advantageous effects.

Particularly preferred pretreatment agents used according to the present invention are characterized in that they contain at least one 4-morpholinomethyl-substituted silicone that comprises structural units of formula (VII)

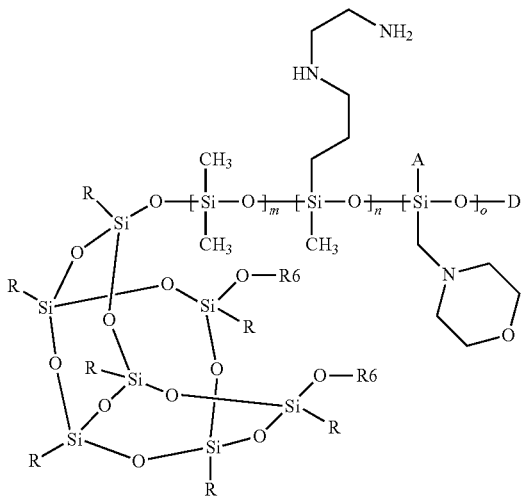

(VII)

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH₃)₃, —Si(CH₃)₂OH, —Si(CH₃)₂OCH₃ group, R denotes a 4-morpholinomethyl residue, R6 denotes —H or the grouping

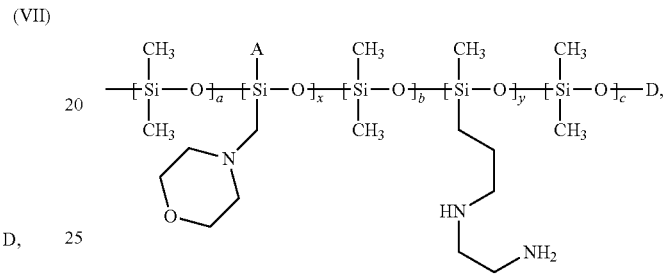

where the siloxane units m, n, and o resp. a, b, c, x, and y are present in statistically distributed fashion.

Pretreatment agents used particularly preferably according to the present invention contain at least one silicone of the following formula (VII a)

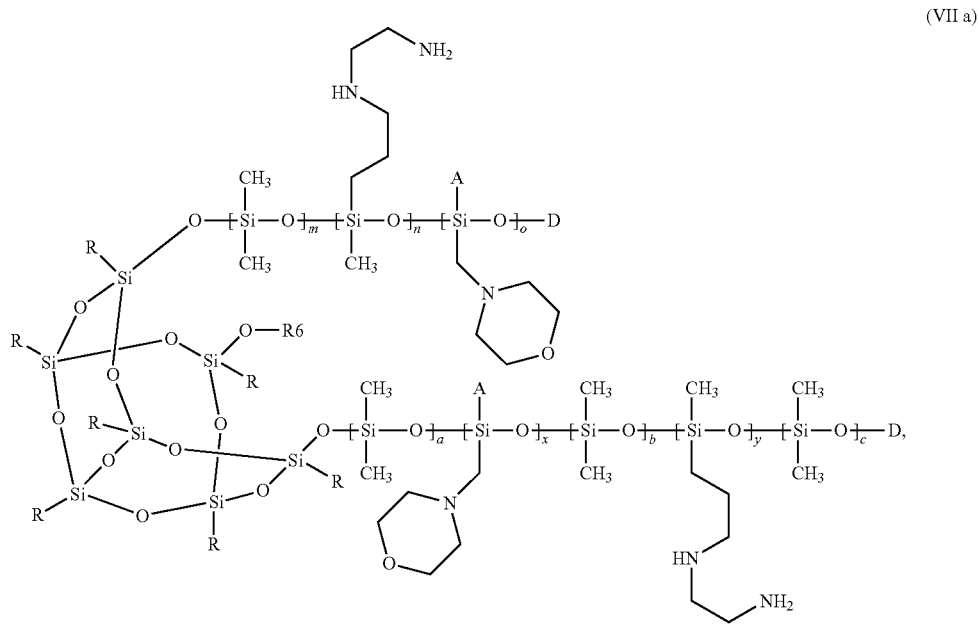

(VII a)

with the definitions as for formula (VII).

Very particularly preferred pretreatment agents used according to the present invention contain at least one silicone of the following formula (VII b)

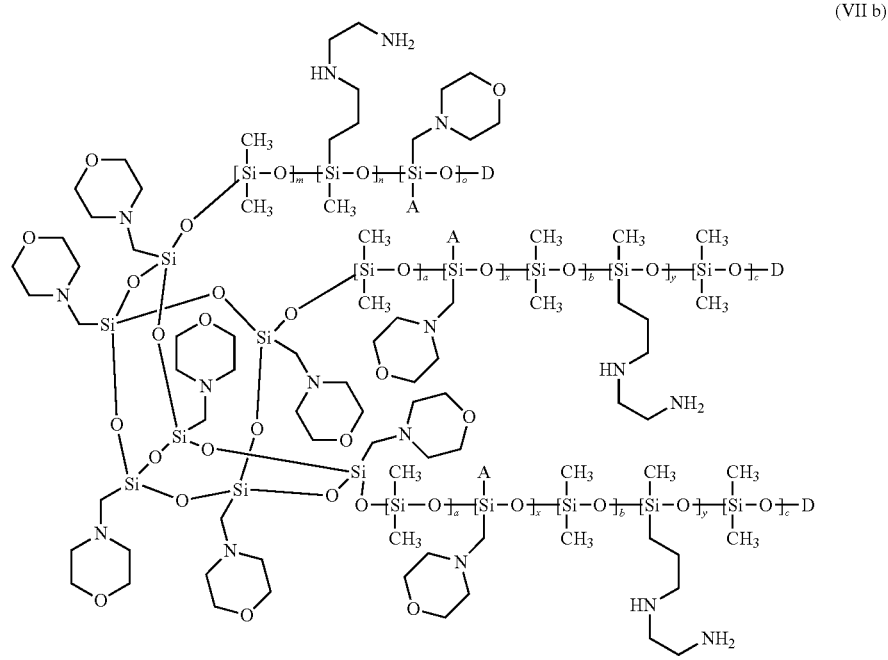

(VII b)

with the definitions as for formula (VII).

In formulas (VII), (VII a), and (VII b), the bridging oxygen atoms between the morpholinomethyl-substituted silicon atoms can also be supplemented by an -[—Si(CH$_3$)$_2$—O]$_m$ grouping, i.e. an oligomer or polymer of structural unit (I). Corresponding pretreatment agents used according to the present invention are those which contain at least one 4-morpholinomethyl-substituted silicone that comprises structural units of formula (VIII)

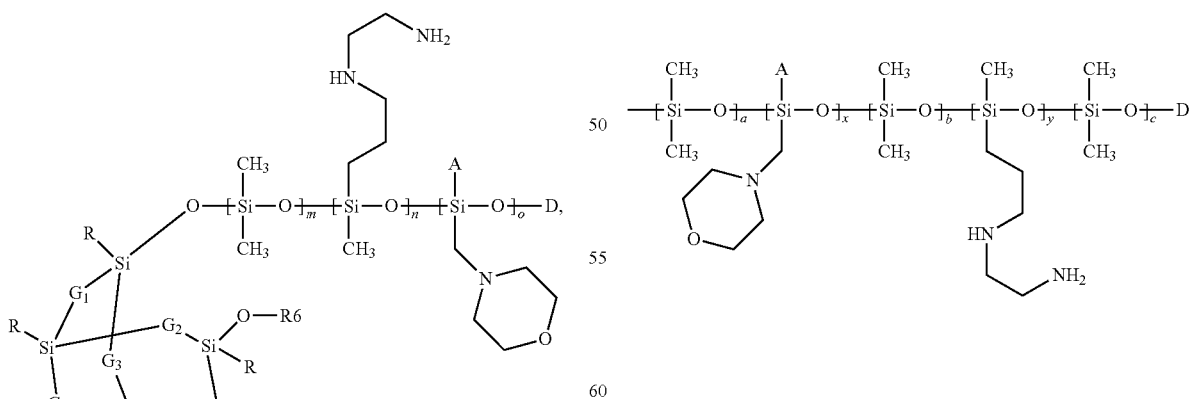

(VIII)

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, G1 to G9 mutually independently denote —O— or an -[—Si(CH$_3$)$_2$—O]$_m$ group where m=1 to about 200, R denotes a 4-morpholinomethyl residue, R6 denotes —H or the grouping where the siloxane units m, n, and o resp. a, b, c, x, and y are present in statistically distributed fashion.

Particularly preferred pretreatment agents used according to the present invention contain at least one silicone of the following formula (VIII a)

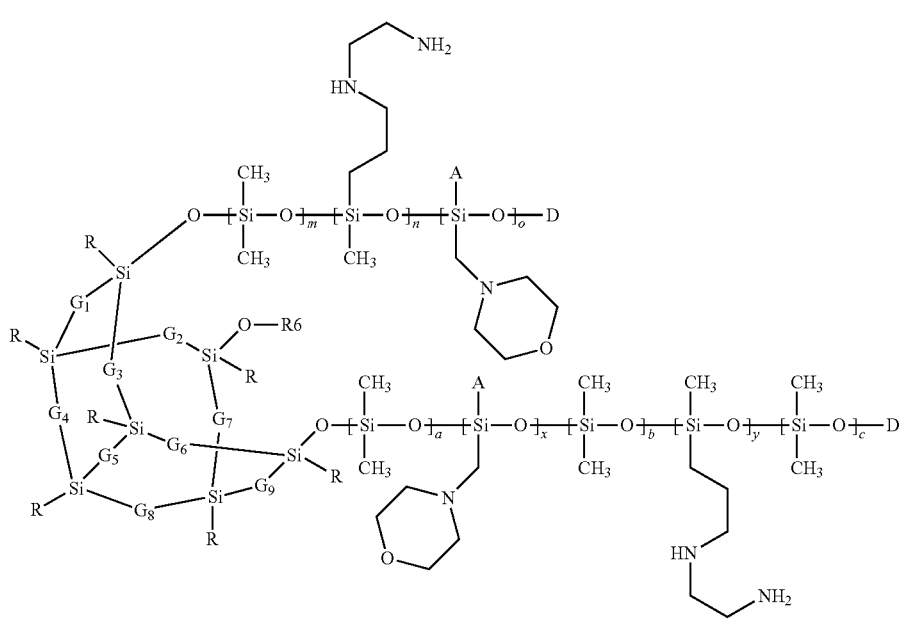

(VIIIa)

with the definitions as for formula (VIII).

Very particularly preferred pretreatment agents used according to the present invention contain at least one silicone of the following formula (VIII b)

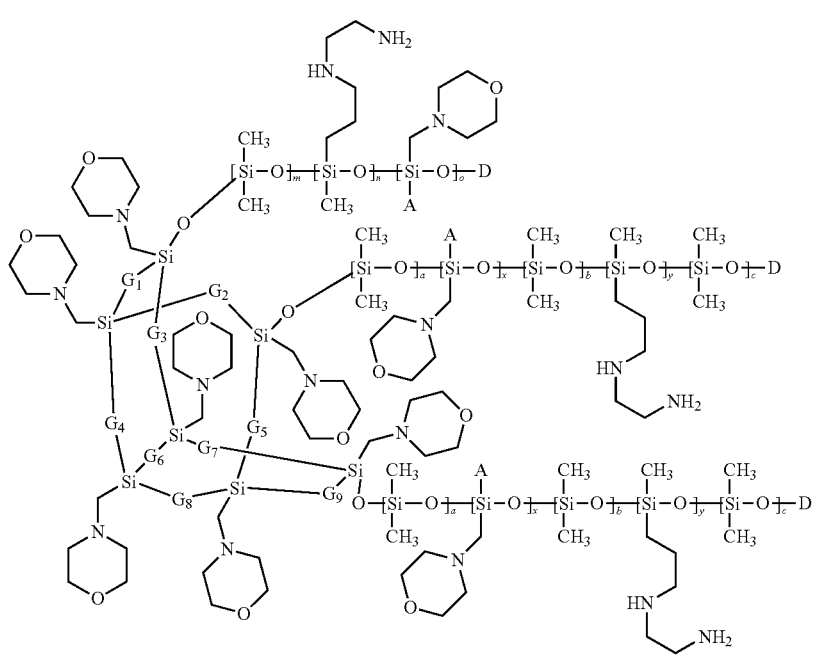

(VIIIb)

with the definitions as for formula (VIII).

Regardless of which special 4-morpholinomethyl-substituted silicone is contained in the pretreatment agents used according to the present invention, pretreatment agents that contain a 4-morpholinomethyl-substituted silicone in which more than about 50 mol % of the structural units are dimethylsiloxy units, i.e. in which structural unit (I) makes up at least about half of all structural units of the silicone used, are preferred for the method according to the present invention.

In other words, silicones in which m>(n+o) resp. (a+b+c)>(n+o), are preferred.

Even further preferred pretreatment agents used according to the present invention contain a 4-morpholinomethyl-substituted silicone in which more than about 87.5 mol % of the structural units are dimethylsiloxy units, i.e. in which structural unit (I) makes up more than about 875 thousandths of all structural units of the silicone used.

In other words, silicones in which m>8(n+o) resp. (a+b+c)>8(n+o), are preferred.

Even further preferred pretreatment agents used according to the present invention contain a 4-morpholinomethyl-substituted silicone in which more than about 96 mol % of the structural units are dimethylsiloxy units, i.e. in which structural unit (I) makes up at least about ninety-six hundredths of all structural units of the silicone used.

In other words, silicones in which m>25(n+o) resp. (a+b+c)>25(n+o), are preferred.

Even further preferred pretreatment agents used according to the present invention contain a 4-morpholinomethyl-substituted silicone in which more than about 98.7 mol % of the structural units are dimethylsiloxy units, i.e. in which structural unit (I) makes up at least about nine hundred eighty-seven thousandths of all structural units of the silicone used.

In other words, silicones in which m>77(n+o) resp. (a+b+c)>77(n+o), are preferred.

Even further preferred pretreatment agents used according to the present invention contain a 4-morpholinomethyl-substituted silicone in which more than about 99.5 mol % of the structural units are dimethylsiloxy units, i.e. in which structural unit (I) makes up at least about nine hundred ninety-five thousandths of all structural units of the silicone used.

In other words, silicones in which m>200(n+o) resp. (a+b+c)>200(n+o), are preferred.

In summary, preferred pretreatment agents used according to the present invention are characterized in that they contain at least one 4-morpholinomethyl-substituted silicone in which m>(n+o) resp. (a+b+c)>(n+o), by preference
m>8(n+o) resp. (a+b+c)>8(n+o), particularly preferably
m>25(n+o) resp. (a+b+c)>25(n+o), more preferably
m>77(n+o) resp. (a+b+c)>77(n+o), and in particular
m>200(n+o) resp. (a+b+c)>200(n+o).

A further method preferred according to the present invention is characterized in that the pretreatment agent used in step a) contains hydroxy-terminated 4-morpholinomethyl-substituted silicone(s) in which the molar ratio of hydroxy to alkoxy is in the range of from about 0.2:1 to about 0.4:1, preferably in the range of from about 1:0.8 to about 1:1.1.

A further method preferred according to the present invention is characterized in that the weight-average molar mass of the 4-morpholinomethyl-substituted silicone of formula (V) used in step a) is in the range of from about 2000 to 1,000,000 gmol$^{-1}$, preferably in the range of from about 5000 to about 200,000 gmol$^{-1}$.

The average molar masses of amino-substituted silicones are measurable, for example, by gel permeation chromatography (GPC) at room temperature in polystyrene. Styragel μ columns can be selected as columns, THF as an eluent, and 1 ml/min as a flow rate. Detection is accomplished preferably by refractometry using a UV meter.

4-Morpholinomethyl-substituted silicones of formula (V) that are particularly preferred according to the present invention are contained in the raw material Belsil ADM 8301 E (ex Wacker Silicones) under the name Amodimethicone/Morpholinomethyl Silsesquioxane. Belsil ADM 8301 E represents a microemulsion and is made up of the following constituents: Amodimethicone/Morpholinomethyl Silsesquioxane (10 wt %); Trideceth-5 (5 wt %); glycerol (2.5 wt %); phenoxyethanol (0.45 wt %); and water (82.05 wt %).

It has become apparent that the method according to the present invention can be further improved if specific nonionic components are likewise contained in the pretreatment agents used according to the present invention. These nonionic components moreover have positive effects on the shelf stability of the pretreatment agents used according to the present invention. Nonionic components that are particularly suitable here are ethoxylates of decanol, undecanol, dodecanol, tridecanol, myristyl alcohol, cetyl alcohol, and/or stearyl alcohol. Ethoxylated tridecanols have proven to be particularly suitable, and are incorporated with particular preference into the pretreatment agents used according to the present invention. Branched ethoxylated tridecanols are particularly preferred, in particular branched tridecanols having from about 3 to about 5 ethylene oxide units in the molecule. Pretreatment agents used particularly preferably according to the present invention contain, based in each case on their weight, about 0.001 to about 5 wt %, by preference about 0.005 to about 3.5 wt %, particularly preferably about 0.01 to about 2 wt %, more preferably about 0.05 to about 1 wt %, and in particular about 0.1 to about 0.5 wt % branched ethoxylated tridecanol, particularly preferably about 0.001 to about 5 wt %, by preference about 0.005 to about 3.5 wt %, particularly preferably about 0.01 to about 2 wt %, more preferably about 0.05 to about 1 wt %, and in particular about 0.1 to about 0.5 wt % branched ethoxylated tridecanol having from about 3 to about 5 ethylene oxide units in the molecule.

Further surfactants and emulsifier agents are preferably not contained, or are contained only in small quantities, in the pretreatment agents used according to the present invention. Pretreatment agents preferably used according to the present invention contain, based on the total weight of the agent, from about 0.001 to a maximum of about 6 wt % surfactant(s), the aforementioned ethoxylates of decanol, undecanol, dodecanol, tridecanol, myristyl alcohol, cetyl alcohol, and/or stearyl alcohol being included.

The pretreatment agents used according to the present invention are by preference of low viscosity, i.e. are formulated with a viscosity (measured at 20° C.) in the range of from about 10 to about 2000 mPas, preferably about 20 to about 1000 mPas, particularly preferably about 50 to about 800 mPas. It has moreover been found that thickening polymers can attenuate the effect according to the present invention, so that preferred pretreatment agents used according to the present invention are characterized in that they contain thickening polymers in a total quantity of ≤about 2.5 wt %, by preference ≤about 1 wt %, more preferably ≤about 0.5 wt %, and in particular ≤about 0.01 wt %, based in each case on the weight of the pretreatment agent.

The pretreatment agents used according to the present invention can contain further ingredients. It is preferred in this context to use polyvalent alcohols that have moisture-donating properties. Pretreatment agents used according to the present invention that contain at least one polyvalent alcohol, preferably selected from the group of sorbitol and/or glycerol and/or 1,2-propylene glycol or mixtures thereof, in a total quantity of from about 0.05 to about 15 wt %, by preference about 0.1 to about 10 wt %, particularly preferably about 0.15 to about 5 wt %, and in particular about 0.15 to about 1 wt %, based in each case on the weight of the pretreatment agent, are preferred here. For specific utilization sectors it can be advantageous to use only one of the three aforementioned preferred polyvalent alcohols. In most cases, glycerol is preferred. Mixtures of two of the three polyvalent alcohols, or of all three polyvalent alcohols, can nevertheless be preferred in other utilization sectors. A mixture of glycerol, sorbitol, and 1,2-propylene glycol at a weight ratio of about 1:(0.5-1):(0.1-0.5) has proven particularly advantageous here.

Besides sorbitol, glycerol, and 1,2-propylene glycol, further polyvalent alcohols that are suitable are those having at least 2 OH groups, by preference mannitol, xylitol, polyethylene glycol, polypropylene glycol, and mixtures thereof.

Among these compounds those having 2 to 12 OH groups, and in particular those having 2, 3, 4, 5, 6, or 10 OH groups, are preferred.

Polyhydroxy compounds having 2 OH groups are, for example, glycol ($CH_2(OH)CH_2OH$) and other 1,2-diols such as $H-(CH_2)_n-CH(OH)CH_2OH$ where n=2, 3, 4, 5, 6, 7, 8, 9, 10, 11, 12, 13, 14, 15, 16, 17, 18, 19, 20. 1,3-Diols such as $H-(CH_2)_n-CH(OH)CH_2CH_2OH$, where n=1, 2, 3, 4, 5, 6, 7, 8, 9, 10, 11, 12, 13, 14, 15, 16, 17, 18, 19, 20, are also usable according to the present invention. The (n,n+1)-resp. (n,n+2)-diols having non-terminal OH groups can likewise be used. Important representatives of polyhydroxy compounds having 2 OH groups are also the polyethylene and polypropylene glycols. Further preferred polyvalent alcohols that can be used are, for example, xylitol, propylene glycols, polyethylene glycols, in particular those having average molecular weights of from about 200 to about 800. It is particularly preferred to use glycerol, so that agents that contain no other polyvalent alcohols besides glycerol are particularly preferred.

The use of specific care-providing substances in the pretreatment agents of the method according to the present invention is preferred in terms of pretreatment prior to an oxidative hair treatment.

Pretreatment agents preferably used according to the present invention are characterized in that they additionally contain care-providing substance(s) in a total quantity of from about 0.001 to about 10 wt %, by preference about 0.005 to about 7.5 wt %, particularly preferably about 0.01 to about 5 wt %, and in particular about 0.05 to about 2.5 wt %, based in each case on the total weight of the pretreatment agent. Preferred care-providing substance(s) are selected from at least one of the groups recited below:
  i. L-carnitine and/or salts thereof;
  ii. taurine and/or salts thereof;
  iii. niacinamide;
  iv. ubiquinone;
  v. ectoin;
  vi. vitamins;
  vii. flavonoids.

Pretreatment agents used according to the present invention can particularly preferably contain one or more amino acids as a further ingredient. Amino acids usable particularly preferably according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide (L-alliine), L-trans-4-hydroxyproline, L-5-oxoproline (L-pyroglutamic acid), L-phosphoserine, creatine, 3-methyl-L-histidine, L-ornithine; both the individual amino acids and mixtures can be used.

Preferred pretreatment agents used according to the present invention contain one or more amino acids in narrower quantity ranges. Pretreatment agents used according to the present invention are characterized here in that they contain as a care-providing substance from about 0.01 to 5 wt %, by preference about 0.02 to about 2.5 wt %, particularly preferably about 0.05 to about 1.5 wt %, more preferably about 0.075 to about 1 wt %, and in particular about 0.1 to about 0.25 wt % amino acid(s), by preference from the group of glycine and/or alanine and/or valine and/or lysine and/or leucine and/or threonine, based in each case on the total weight of the pretreatment agent.

The pretreatment agent used according to the present invention can be formulated as a low-viscosity water-based emulsion, a spray, a cream, gel, lotion, paste, shampoo, or conditioner.

The method according to the present invention encompasses the application of a pretreatment agent onto keratinic fibers, and an oxidative coloring treatment subsequent thereto within a time period of from about one second to about 24 hours.

A great advantage of the pretreatment agents used in step a) is that they are effective not only when utilized immediately prior to oxidative hair treatment, but instead can be utilized up to about 24 hours previously with no risk of attenuation of the effect due to external influences. It is thereby possible, for example, to carry out step a) of the method according to the present invention in the morning after shampooing, and to perform the oxidative hair treatment only in the evening.

Methods preferred according to the present invention are characterized in that the time period between method steps a) and b) is from about 2 seconds to about 20 minutes, preferably about 30 seconds to about 10 minutes, particularly preferably about 1 to about 5 minutes.

Further methods preferred according to the present invention are characterized in that the pretreatment agent applied in method step a) is allowed to act on the hair for a time period of from about 2 seconds to about 120 minutes, preferably about 5 seconds to about 10 minutes, before method step b) is begun.

Further methods preferred according to the present invention are characterized in that the pretreatment agent applied in method step a) is allowed to act on the hair for a time period of from about 2 seconds to about 120 minutes, preferably about 5 seconds to about 10 minutes, before at least one of the following method steps a)i, which occur before method step b), is begun:
  rinsing out the hair;
  allowing the hair to air-dry;
  blow-drying the hair;
  drying the hair with a drying hood;
  drying the hair with a towel.

The drying operation can occur at a temperature of from about 20° C. to about 150° C.

Preferably the drying operation resp. operations are not preceded by rinsing out of the hair. It can, however, also be preferred according to the present invention first to rinse out the hair after step a) and then to dry it before the coloring step b) occurs.

The method according to the present invention is furthermore characterized in that step b) encompasses the application of a hair coloring agent that contains at least one oxidation dye precursor of the developer type and at least one oxidation dye precursor of the coupler type, as well as at least one oxidizing agent.

The hair coloring agents used in step b) of this method according to the present invention therefore contain as a first obligatory ingredient at least one oxidizing agent. Preferred oxidizing agents are selected from peroxo compounds, preferably selected from hydrogen peroxide, a solid addition compound of hydrogen peroxide with inorganic or organic compounds, for example sodium perborate, sodium percarbonate, magnesium percarbonate, sodium percarbamide, polyvinylpyrrolidone.n $H_2O_2$ (n is a positive number greater than 0), urea peroxide, and melamine peroxide, furthermore selected from diammonium peroxodisulfate (also referred to as ammonium persulfate), disodium peroxodisulfate (also referred to as sodium persulfate), and dipotassium peroxodisulfate (also referred to as potassium persulfate), and from mixtures of these oxidizing agents. Oxidizing agents used with very particular preference according to the present invention are aqueous hydrogen peroxide solutions. The concentration of a hydrogen peroxide solution is determined on the one hand by regulatory provisions and on the other hand by the desired effect; 6- to 12-weight-percent solutions in water are preferably used. Methods preferred according to the present invention are characterized in that the hair coloring agents used in step b) contain, based on their weight, about 0.5 to about 12 wt %, preferably about 2 to about 10 wt %, particularly preferably about 3 to about 6 wt % hydrogen peroxide (calculated as 100% $H_2O_2$).

Oxidative coloring processes on keratin fibers usually proceed in an alkaline environment. In order to minimize stress on the keratin fibers and also on the skin, however, it is not desirable to establish too high a pH. It is therefore preferred if the pH of the hair coloring agent used in step b) is in the range of from about 7 to about 11, in particular in the range of from about 8 to about 10.5. The pH values for purposes of the present invention are pH values that have been measured at a temperature of 22° C.

The alkalizing agents usable according to the present invention in order to establish the preferred pH can be selected from the group of ammonia, basic amino acids, alkali hydroxides, alkanolamines, alkali metal metasilicates, alkali phosphates, and alkali hydrogen phosphates. Lithium, sodium, potassium preferably serve as alkali metal ions, in particular sodium or potassium.

The basic amino acids usable as alkalizing agents are preferably selected from the group of L-arginine, D-arginine, D,L-arginine, L-lysine, D-lysine, D,L-lysine, particularly preferably L-arginine, D-arginine, D,L-arginine used as an alkalizing agent for purposes of the invention.

The alkali hydroxides usable as alkalizing agents are preferably selected from the group of sodium hydroxide and potassium hydroxide.

The alkanolamines usable as alkalizing agents are preferably selected from primary amines having a $C_2$ to $C_6$ alkyl basic structure that carries at least one hydroxyl group. Particularly preferred alkanolamines are selected from the group that is constituted from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines very particularly preferred according to the present invention are selected from the group of: 2-aminoethan-1-ol, 2-amino-2-methylpropan-1-ol, and 2-amino-2-methylpropane-1,3-diol.

The use of hydrogen peroxide or addition products thereof with organic resp. inorganic compounds is often insufficient for a coloring operation that requires considerable lightening of very dark hair. A combination of hydrogen peroxide and peroxodisulfate salts (persulfate salts) is generally used in such cases. Preferred persulfate salts are ammonium peroxydisulfate, potassium peroxydisulfate, sodium peroxydisulfate, and mixtures thereof.

The at least one persulfate salt is contained preferably in a total quantity of from about 0.1 to about 25 wt %, particularly preferably in a total quantity of from about 1 to about 15 wt %, based on the weight of the ready-to-use coloring agent.

The coloring agents used in step b) of the method according to the present invention contain as further obligatory ingredients at least one oxidation dye precursor of the developer type and at least one oxidation dye precursor of the coupler type.

Oxidation dye precursors can be divided in terms of their reaction behavior into two categories: the so-called developer components and coupler components.

Coupler components alone do not produce any significant color in the context of oxidative coloring, but instead always require the presence of developer components. Developer components can form, with themselves, the actual dye.

The developer and coupler components are usually used in free form. In the case of substances having amino groups, however, it can be preferred to use them in salt form, in particular in the form of the hydrochlorides or hydrobromides or the sulfates.

It has been found, surprisingly, that hair coloring results with particularly good washing fastness could be achieved with the method according to the present invention using at least one oxidation dye precursor of the developer type and at least one oxidation dye precursor of the coupler type. A particularly good improvement in washing fastness was observed for formulations having the developer/coupler combination 1-hydroxyethyl-4,5-diaminopyrazole/3-aminophenol. The reduction in hair damage was also surprisingly large.

Particularly preferred developer components are selected from at least one compound of the group that is constituted from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, the physiologically acceptable salts of these compounds, and mixtures of these developer components and developer component salts.

Very particularly preferred developer components are selected from 4,5-diamino-1-(2-hydroxyethyl)pyrazole, p-toluoylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and mixtures of these compounds as well as physiologically acceptable salts thereof. 4,5-Diamino-1-(2-hydroxyethyl)pyrazole and physiologically acceptable salts thereof are extraordinarily preferred.

The developer components are used preferably in a total quantity of from about 0.005 to about 10 wt %, particularly preferably about 0.1 to about 5 wt %, based in each case on the weight of the ready-to-use coloring agent.

The term "ready-to-use coloring agent" is understood for purposes of this Application as the mixture of all oxidation dye precursors and all oxidizing agents, optionally in combination with a suitable cosmetic carrier, e.g. a cream base, as well as optionally in combination with at least one substantive dye.

Coupler components for purposes of the invention allow at least one chemical residue of the coupler to be substituted with the oxidized form of the developer component, in which context a covalent bond forms between the coupler component and developer component. Couplers are preferably cyclic compounds that carry on the cycle at least two groups selected from (i) optionally substituted amino groups, and/or (ii) hydroxyl groups. If the cyclic compound is a six-membered ring (preferably aromatic), the aforesaid groups are then located preferably in the ortho or meta position with respect to one another.

Preferred methods according to the present invention are characterized in that the at least one oxidation dye precursor of the coupler type is selected from one of the following classes:

3-aminophenol (m-aminophenol) and/or derivatives thereof, 3-aminoaniline (m-diaminobenzene) and/or derivatives thereof, 2-aminoaniline (1,2-diaminobenzene; o-diaminobenzene) and/or derivatives thereof, 2-aminophenol (o-aminophenol) and/or derivatives thereof, naphthalene derivatives having at least one hydroxy group, di-resp. trihydroxybenzene and/or derivatives thereof, pyridine derivatives,
pyrimidine derivatives,
monohydroxyindole derivatives and/or monoaminoindole derivatives,
monohydroxyindoline derivatives and/or monoaminoindoline derivatives
pyrazolone derivatives such as e.g. 1-phenyl-3-methylpyrazol-5-one,
morpholine derivatives such as e.g. 6-hydroxybenzomorpholine or 6-aminobenzomorpholine,
quinoxaline derivatives such as e.g. 6-methyl-1,2,3,4-tetrahydroquinoxaline.

Mixtures of two or more compounds from one or more of these classes are likewise preferred according to the present invention in the context of this embodiment.

Additional coupler components particularly preferred according to the present invention are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl) amino-2-methylphenol, 2,4-dichloro-3-aminophenol, 2-aminophenol, 3-phenylenediamine, 2-(2,4-diaminophenoxy) ethanol, 1,3-bis-(2,4-diaminophenoxy)propane, 1-methoxy-2-amino-4-(2'-hydroxyethylamino)benzene (=2-amino-4-hydroxyethylaminoanisole), 1,3-bis-(2,4-diaminophenyl) propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl) amino]-2-methoxy-5-methylphenyl}amino)ethanol, 2-({3-[(2-hydroxyethyl)amino]-4,5-dimethylphenyl}amino) ethanol 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynapthalene, 4-hydroxyindole, 6-hydroxyindole, 7-hydroxyindole, 4-hydroxyindoline, 6-hydroxyindoline, 7-hydroxyindoline, or mixtures of these compounds, or the physiologically acceptable salts of the aforesaid compounds.

Very particularly preferred in this context, are 3-aminophenol, resorcinol, 2-methylresorcinol, 5-amino-2-methylphenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, and 1-naphthol, as well as physiologically acceptable salts thereof and mixtures of the components recited.

The at least one coupler component is used preferably in a total quantity of from about 0.005 to about 20 wt %, preferably about 0.1 to about 5 wt %, and extraordinarily preferably about 0.3 to about 2.5 wt %, based in each case on the weight of the ready-to-use oxidative coloring agent.

The following combinations of oxidation dye precursors of the developer type and of the coupler type are particularly preferred in the context of the present invention, where the amine compounds and the nitrogen heterocycles can also be present in the form of their physiologically acceptable salts:

p-toluoylenediamine/resorcinol;
p-toluoylenediamine/2-methylresorcinol;
p-toluoylenediamine/5-amino-2-methylphenol;
p-toluoylenediamine/3-aminophenol;
p-toluoylenediamine/2-(2,4-diaminophenoxy)ethanol;
p-toluoylenediamine/1,3-bis-(2,4-diaminophenoxy)propane;
p-toluoylenediamine/1-methoxy-2-amino-4-(2-hydroxyethylamino)benzene;
p-toluoylenediamine/2-amino-3-hydroxypyridine;
p-toluoylenediamine/1-naphthol;
2-(2-hydroxyethyl)-p-phenylenediamine/resorcinol;
2-(2-hydroxyethyl)-p-phenylenediamine/2-methylresorcinol;
2-(2-hydroxyethyl)-p-phenylenediamine/5-amino-2-methylphenol;
2-(2-hydroxyethyl)-p-phenylenediamine/3-aminophenol;
2-(2-hydroxyethyl)-p-phenylenediamine/2-(2,4-diaminophenoxy)ethanol;
2-(2-hydroxyethyl)-p-phenylenediamine/1,3-bis-(2,4-diaminophenoxy)propane;
2-(2-hydroxyethyl)-p-phenylenediamine/1-methoxy-2-amino-4-(2-hydroxyethylamino)benzene;
2-(2-hydroxyethyl)-p-phenylenediamine/2-amino-3-hydroxypyridine;
2-(2-hydroxyethyl)-p-phenylenediamine/1-naphthol;
2-methoxymethyl-p-phenylenediamine/resorcinol;
2-methoxymethyl-p-phenylenediamine/2-methylresorcinol;
2-methoxymethyl-p-phenylenediamine/5-amino-2-methylphenol;
2-methoxymethyl-p-phenylenediamine/3-aminophenol;
2-methoxymethyl-p-phenylenediamine/2-(2,4-diaminophenoxy)ethanol;
2-methoxymethyl-p-phenylenediamine/1,3-bis-(2,4-diaminophenoxy)propane;
2-methoxymethyl-p-phenylenediamine/1-methoxy-2-amino-4-(2-hydroxyethylamino)benzene;
2-methoxymethyl-p-phenylenediamine/2-amino-3-hydroxypyridine;
2-methoxymethyl-p-phenylenediamine/1-naphthol;
N-(4-amino-3-methylphenyl)-N-[3-(1H-imidazol-1-yl)propyl]amine/resorcinol;
N-(4-amino-3-methylphenyl)-N-[3-(1H-imidazol-1-yl)propyl]amine/2-methylresorcinol;
N-(4-amino-3-methylphenyl)-N-[3-(1H-imidazol-1-yl)propyl]amine/5-amino-2-methylphenol;
N-(4-amino-3-methylphenyl)-N-[3-(1H-imidazol-1-yl)propyl]amine/3-aminophenol;
N-(4-amino-3-methylphenyl)-N-[3-(1H-imidazol-1-yl)propyl]amine/2-(2,4-diaminophenoxy)ethanol;

N-(4-amino-3-methylphenyl)-N-[3-(1H-imidazol-1-yl)propyl]amine/1,3-bis-(2,4-diaminophenoxy)propane;

N-(4-amino-3-methylphenyl)-N-[3-(1H-imidazol-1-yl)propyl]amine/1-methoxy-2-amino-4-(2-hydroxyethylamino)benzene;

N-(4-amino-3-methylphenyl)-N-[3-(1H-imidazol-1-yl)propyl]amine/2-amino-3-hydroxypyridine;

N-(4-amino-3-methylphenyl)-N-[3-(1H-imidazol-1-yl)propyl]amine/1-naphthol;

4,5-diamino-1-(2-hydroxyethyl)pyrazole/resorcinol;

4,5-diamino-1-(2-hydroxyethyl)pyrazole/2-methylresorcinol;

4,5-diamino-1-(2-hydroxyethyl)pyrazole/5-amino-2-methylphenol;

4,5-diamino-1-(2-hydroxyethyl)pyrazole/3-aminophenol;

4,5-diamino-1-(2-hydroxyethyl)pyrazole/2-(2,4-diaminophenoxy)ethanol;

4,5-diamino-1-(2-hydroxyethyl)pyrazole/1,3-bis-(2,4-diaminophenoxy)propane;

4,5-diamino-1-(2-hydroxyethyl)pyrazole 1-methoxy-2-amino-4-(2-hydroxyethylamino)benzene;

4,5-diamino-1-(2-hydroxyethyl)pyrazole/2-amino-3-hydroxypyridine;

4,5-diamino-1-(2-hydroxyethyl)pyrazole/1-naphthol.

The combinations 4,5-diamino-1-(2-hydroxyethyl)pyrazole/3-aminophenol and p-toluoylenediamine/3-aminophenol are particularly preferred according to the present invention. The combination 4,5-diamino-1-(2-hydroxyethyl)pyrazole/3-aminophenol is extraordinarily preferred, in particular in terms of improving washing fastness.

In order to achieve balanced and subtle toning, it is preferred according to the present invention if further color-imparting components are contained in the coloring agent that is used in step b) of the method according to the present invention.

In a further embodiment, the agents used in step b) of this variant of the method according to the present invention can additionally contain at least one substantive dye. These are dyes that absorb directly onto the hair and do not require an oxidizing process for formation of the color. Substantive dyes are usually nitrophenylenediamines, nitroaminophenols, azo dyes, anthraquinones, or indophenols.

A further method preferred according to the present invention is characterized in that the coloring agent applied in step b) is rinsed off the fibers after a period of from about 5 to about 60 minutes, preferably about 30 to about 45 minutes.

The coloring agent used in the method according to the present invention in step b) is preferably produced from a two-component agent, where one component contains the oxidation dye precursors and the other component contains the oxidizing agent or agents. The ready-to-use coloring agent for step b) is then produced by mixing the two components directly before the application step b). A separation into multi-component systems is advisable in particular when incompatibilities of the ingredients are expected or are a concern.

A further subject of the present invention is the use of at least one 4-morpholinomethyl-substituted silicone of formula (V),

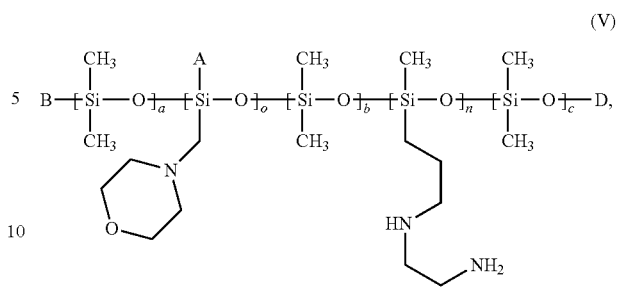

in which
A denotes a structural unit (I), (II), or (III) bound via —O—

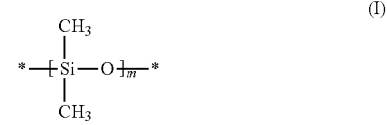

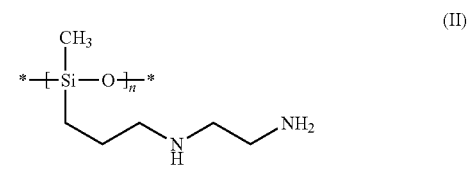

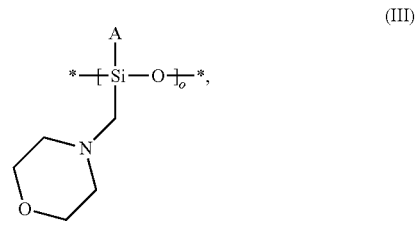

or an oligomeric or polymeric residue bound via —O— containing structural units of formulas (I), (II), or (III), or half of an oxygen atom connecting to a structural unit (III), or denotes —OH,
* denotes a bond to one of the structural units (I), (II), or (III), or denotes a terminal group B (Si-bound) or D (O-bound),
B denotes an —OH, —O—Si(CH$_3$)$_3$, —O—Si(CH$_3$)$_2$OH, —O—Si(CH$_3$)$_2$OCH$_3$ group,
D denotes an —H, —Si(CH$_3$)$_3$, —Si(CH$_3$)$_2$OH, —Si(CH$_3$)$_2$OCH$_3$ group,
a, b, and c denote integers from about 0 to about 990, with the provision that a+b+c>0,
m, n, and o denote integers from about 2 to about 990,
to improve the washing fastness of an oxidative hair color that has been obtained from at least one oxidation dye precursor of the developer type and at least one oxidation dye precursor of the coupler type as well as at least one oxidizing agent.

A use preferred according to the present invention is characterized in that the oxidative hair color was obtained using a hair coloring agent that contains the combination of 4,5-diamino-1-(2-hydroxyethyl)pyrazole and 3-aminophenol, as well as at least one oxidizing agent.

The statements made about the preferred embodiments of the method according to the present invention apply mutatis mutandis to the uses preferred according to the present invention.

EXEMPLIFYING EMBODIMENTS

Example 1

Hair skeins were immersed for one minute into an aqueous emulsion of a 4-morpholinomethyl-substituted silicone of formula (V) that contained 0.01 wt % 4-morpholinomethyl-substituted silicone(s) of formula (V) and 0.005 wt % branched Trideceth-5, furthermore 0.006 wt % glycerol, and water to 100 wt %, and then blow-dried.

A freshly prepared coloring cream/oxidizing agent mixture was then applied onto the skeins and allowed to act for 30 minutes. The coloring agent was then rinsed out with water. The skeins were blow-dried for the color measurements. The combing tests were performed on skeins that had been combed three times after rinsing out the coloring cream/oxidizing agent mixture.

| Color creams (quantities indicated in wt %) | | | |
|---|---|---|---|
| Ingredient | 5-0 | 6-88 | 12-0 |
| 1-Hydroxyethyl-4,5-Diamino Pyrazole Sulfate | — | 1.5 | |
| Toluene-2,5-Diamine Sulfate | 1.4 | | 0.02 |
| 3-Aminophenol | 0.2 | 0.6 | |
| Resorcinol | 0.7 | | |
| 2-Amino-4-Hydroxyethylaminoanisole Sulfate (1-methoxy-2-amino-4-(2'-hydroxyethylamino)benzene sulfate) | 0.02 | | 0.02 |
| 4-Amino-2-Hydroxytoluene | | 0.3 | 0.01 |
| 4-Amino-m-Cresol | | 0.18 | |
| Cetearyl Alcohol | 14 | 14 | 14 |
| Glyceryl Stearate | 1.4 | 1.4 | 1.4 |
| Ammonium Hydroxide | 3.4 | 3.4 | 6.8 |
| Ceteareth-20 | 3.5 | 3.5 | 3.5 |
| Octyldodecanol | 1 | 1 | 1 |
| Sodium Laureth Sulfate | 0.5 | 0.5 | 0.5 |
| 1,3-Butylene glycol | 3.5 | 3.5 | 3.5 |
| Sodium Cetearyl Sulfate | 1.0 | 1.0 | 1.0 |
| Ethanolamine | 0.7 | 0.6 | |
| Oleic Acid | 0.1 | 0.1 | 0.1 |
| Perfume (Fragrance) | 0.5 | 0.5 | 0.5 |
| Potassium Stearate | 0.5 | 0.5 | 0.5 |
| Sodium Sulfite | 0.2 | 0.2 | 0.2 |
| Tetrasodium EDTA | 0.3 | 0.3 | 0.3 |
| Carbomer | 0.3 | 0.3 | 0.3 |
| Polyquaternium-39 (ex Merquat 3330) | 0.05 | 0.05 | 0.05 |
| Potassium Hydroxide | 0.06 | 0.08 | 0.08 |
| Ascorbic Acid | 0.02 | 0.02 | 0.02 |
| Linoleamidopropyl PG-Dimonium Chloride Phosphate | 0.1 | 0.1 | 0.1 |
| Sodium Sulfate | 0.1 | 0.1 | 0.1 |
| Citric Acid | 0.002 | 0.002 | 0.002 |
| CI 77891 (Titanium Dioxide) | 0.3 | 0.3 | 0.3 |
| Aqua (Water, Eau) | to 100 | to 100 | to 100 |

The color creams 5-0 and 6-88 listed above were mixed at a 1:1 weight ratio with developer dispersion no. 1 (presented below) to yield respective ready-to-use coloring agents. The color cream 12-0 listed above was mixed at a 1:1 weight ratio with developer dispersion no. 2 (presented below) to yield a ready-to-use coloring agent. The respective coloring agent was then applied onto the test skeins, specifically at a rate of 4 g coloring agent per gram of hair for the tests of combability, splitting, hair breakage, and sensory qualities, and 5 g coloring agent per gram of hair for the washing fastness tests. The coloring agents remained on the skeins for 30 minutes in each case. The skeins were then rinsed out for 2 minutes using warm (32° C.) tap water at a flow rate of 0.5 liter per minute.

| Developer dispersions used (quantities indicated in wt %) | | |
|---|---|---|
| Ingredients | No. 1 | No. 2 |
| Cetearyl Alcohol | 4.0 | 4.0 |
| Dipicolinic acid | 0.1 | 0.1 |
| Disodium Pyrophosphate | 0.1 | 0.1 |
| Potassium Hydroxide | 0.1 | 0.1 |
| 1,2-Propylene glycol | 1.0 | 1.0 |
| 1-Hydroxyethane-1,1-Diphosphonic Acid (Etidronic Acid) | 0.1 | 0.1 |
| Paraffinum Liquidum | 0.5 | 0.5 |
| Steartrimonium Chloride | 0.5 | 0.5 |
| Ceteareth-20 | 1.0 | 1.0 |
| $H_2O_2$ (active matter) | 6.0 | 12.0 |
| Water | to 100 | to 100 |

| Wet combability; combing work (mJ) | | | |
|---|---|---|---|
| | untreated (mJ) | pretreated (mJ) (according to the present invention) | Relative change (%) |
| Shade 5-0 | 633 | 396 | 37 |
| Shade 6-88 | 573 | 402 | 30 |
| Shade 12-0 | 694 | 483 | 30 |

| Split count after 20,000 comb strokes (proportion as %) | | | |
|---|---|---|---|
| | untreated | pretreated (according to the present invention) | Relative change (%) |
| Shade 5-0 | 5.6 | 3.2 | 44 |
| Shade 6-88 | 6.5 | 2.7 | 58 |
| Shade 12-0 | 6.2 | 2.6 | 57 |

| Hair breakage after 20,000 comb strokes (proportion as %) | | | |
|---|---|---|---|
| | untreated | pretreated (according to the present invention) | Relative change (%) |
| Shade 5-0 | 4.8 | 2.5 | 48 |
| Shade 6-88 | 4.4 | 2.1 | 52 |
| Shade 12-0 | 4.4 | 2.3 | 49 |

| Sensory evaluation of the hair by trained hairdressers | | |
|---|---|---|
| | untreated | pretreated (according to the present invention) |
| Shade 5-0 | + | ++ |
| Shade 6-88 | + | ++ |
| Shade 12-0 | + | ++ |

As a result of the pretreatment according to the present invention using the 4-morpholinomethyl-substituted silicone of formula (V), hair damage was appreciably reduced as compared with oxidative coloring without a pretreatment according to the present invention, i.e. wet combability was simplified (lower combing work being equivalent to less hair damage), and splitting and hair breakage were reduced by approximately half. The sensory evaluation of the hair by trained hairdressers also confirmed that the hair treated according to the present invention feels softer and smoother than the untreated hair.

Washing fastness after 36 washing cycles (L a b color difference ΔE)

$\Delta E = E_{before\ washing} - E_{after\ washing}$

| | untreated | pretreated (according to the present invention) |
|---|---|---|
| Shade 5-0 | 3.4 | 3.3 |
| Shade 6-88 | 6.8 | 5.4 |

The tests of washing fastness after 36 washing cycles also show that the difference between initial color and color after 36 washing cycles is appreciably less in the case of the hair treated according to the present invention, i.e. less color was washed out than in the case of the untreated hair.

The invention claimed is:

1. A method for oxidative coloring of keratinic fibers, in particular human hair, wherein
   a. a pretreatment agent that comprises at least one 4-morpholinomethyl-substituted silicone of formula (V),

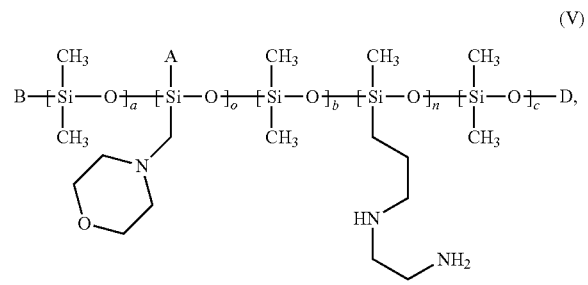
(V)

in which

A denotes a structural unit (I), (II), or (III) bound via —O—

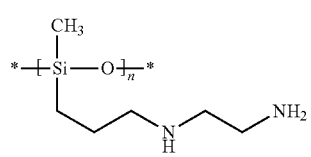
(II)

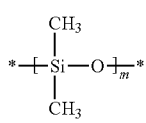
(I)

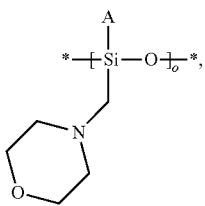
(III)

or an oligomeric or polymeric residue bound via —O— containing structural units of formulas (I), (II), or (III), or half of an oxygen atom connecting to a structural unit (III), or denotes —OH,
   * denotes a bond to one of the structural units (I), (II), or (III), or denotes a terminal group B (Si-bound) or D (O-bound),
   B denotes an —OH, —O—Si(CH$_3$)$_3$, —O—Si(CH$_3$)$_2$OH, —O—Si(CH$_3$)$_2$OCH$_3$ group,
   D denotes an —H, —Si(CH$_3$)$_3$, —Si(CH$_3$)$_2$OH, —Si(CH$_3$)$_2$OCH$_3$ group,
   a, b, and c denote integers from about 0 to about 990, with the provision that a+b+c>0,
   m, n, and o denote integers from about 1 to about 990
is applied onto the keratinic fibers, in particular onto the hair,
   b. subsequently, within a time span of from about one second to about 24 hours after step a), a hair coloring agent is applied onto the keratinic fibers, which agent comprises at least one oxidation dye precursor of the developer type and at least one oxidation dye precursor of the coupler type, as well as at least one oxidizing agent.

2. The method according to claim 1, wherein the pretreatment agent used in step a) comprises at least one 4-morpholinomethyl-substituted silicone of formula (V) in which m>(n+o) resp. (a+b+c)>(n+o).

3. The method according to claim 1, wherein the pretreatment agent used in step a) comprises, based on its weight, 4-morpholinomethyl-substituted silicone(s) in a total quantity of from about 0.001 to about 5 wt %, based on the total weight of the pretreatment agent.

4. The method according to claim 1, wherein the pretreatment agent used in step a) comprises, based on its weight, at least one 4-morpholinomethyl-substituted silicone of formula (V) that respectively comprises at least one of the structural units of formulas (I), (II), and (III), in a total quantity of from about 0.001 to about 5 wt %, based on the total weight of the pretreatment agent.

5. The method according to claim 1, wherein the pretreatment agent used in step a) comprises hydroxy-terminated 4-morpholinomethyl-substituted silicone(s) in which the molar ratio of hydroxy to alkoxy is in the range of from about 0.2:1 to about 0.4:1.

6. The method according to claim 1, wherein the weight-average molar mass of the 4-morpholinomethyl-substituted silicone of formula (V) used in step a) is in the range of from about 2,000 to about 1,000,000 gmol$^{-1}$.

7. The method according to claim 1, wherein the 4-morpholinomethyl-substituted silicone of formula (V) used in step a) is present in the form of an oil-in-water emulsion in which the number-average size of the silicone particles in the emulsion is in the range of from about 3 to about 500 nm.

8. The method according to claim 1, wherein the combination of at least one oxidation dye precursor of the developer type and at least one oxidation dye precursor of the coupler type applied in step b) is selected from at least one of the following combinations, where the amine compounds and the nitrogen heterocycles are optionally present in the form of their physiologically acceptable salts:
p-toluoylenediamine/resorcinol;
p-toluoylenediamine/2-methylresorcinol;
p-toluoylenediamine/5-amino-2-methylphenol;
p-toluoylenediamine/3-aminophenol;
p-toluoylenediamine/2-(2,4-diaminophenoxy)ethanol;
p-toluoylenediamine/1,3-bis(2,4-diaminophenoxy)propane;
p-toluoylenediamine/1-methoxy-2-amino-4-(2-hydroxyethylamino)benzene;
p-toluoylenediamine/2-amino-3-hydroxypyridine;
p-toluoylenediamine/1-naphthol;
2-(2-hydroxyethyl)-p-phenylenediamine/resorcinol;
2-(2-hydroxyethyl)-p-phenylenediamine/2-methylresorcinol;
2-(2-hydroxyethyl)-p-phenylenediamine/5-amino-2-methylphenol;
2-(2-hydroxyethyl)-p-phenylenediamine/3-aminophenol;
2-(2-hydroxyethyl)-p-phenylenediamine/2-(2,4-diaminophenoxy)ethanol;
2-(2-hydroxyethyl)-p-phenylenediamine/1,3-bis(2,4-diaminophenoxy)propane;
2-(2-hydroxyethyl)-p-phenylenediamine/1-methoxy-2-amino-4-(2-hydroxyethylamino)benzene;
2-(2-hydroxyethyl)-p-phenylenediamine/2-amino-3-hydroxypyridine;
2-(2-hydroxyethyl)-p-phenylenediamine/1-naphthol;
2-methoxymethyl-p-phenylenediamine/resorcinol;
2-methoxymethyl-p-phenylenediamine/2-methylresorcinol;
2-methoxymethyl-p-phenylenediamine/5-amino-2-methylphenol;
2-methoxymethyl-p-phenylenediamine/3-aminophenol;
2-methoxymethyl-p-phenylenediamine/2-(2,4-diaminophenoxy)ethanol;
2-methoxymethyl-p-phenylenediamine/1,3-bis(2,4-diaminophenoxy)propane;
2-methoxymethyl-p-phenylenediamine/1-methoxy-2-amino-4-(2-hydroxyethylamino)benzene;
2-methoxymethyl-p-phenylenediamine/2-amino-3-hydroxypyridine;
2-methoxymethyl-p-phenylenediamine/1-naphthol;
N-(4-amino-3-methylphenyl)-N-[3-(1H-imidazol-1-yl)propyl]amine/resorcinol;
N-(4-amino-3-methylphenyl)-N-[3-(1H-imidazol-1-yl)propyl]amine/2-methylresorcinol;
N-(4-amino-3-methylphenyl)-N-[3-(1H-imidazol-1-yl)propyl]amine/5-amino-2-methylphenol;
N-(4-amino-3-methylphenyl)-N-[3-(1H-imidazol-1-yl)propyl]amine/3-aminophenol;
N-(4-amino-3-methylphenyl)-N-[3-(1H-imidazol-1-yl)propyl]amine/2-(2,4-diaminophenoxy)ethanol;
N-(4-amino-3-methylphenyl)-N-[3-(1H-imidazol-1-yl)propyl]amine/1,3-bis(2,4-diaminophenoxy)propane;
N-(4-amino-3-methylphenyl)-N-[3-(1H-imidazol-1-yl)propyl]amine/1-methoxy-2-amino-4-(2-hydroxyethylamino)benzene;
N-(4-amino-3-methylphenyl)-N-[3-(1H-imidazol-1-yl)propyl]amine/2-amino-3-hydroxypyridine;
N-(4-amino-3-methylphenyl)-N-[3-(1H-imidazol-1-yl)propyl]amine/1-naphthol;
4,5-diamino-1-(2-hydroxyethyl)pyrazole/resorcinol;
4,5-diamino-1-(2-hydroxyethyl)pyrazole/2-methylresorcinol;
4,5-diamino-1-(2-hydroxyethyl)pyrazole/5-amino-2-methylphenol;
4,5-diamino-1-(2-hydroxyethyl)pyrazole/3-aminophenol;
4,5-diamino-1-(2-hydroxyethyl)pyrazole/2-(2,4-diaminophenoxy)ethanol;
4,5-diamino-1-(2-hydroxyethyl)pyrazole/1,3-bis(2,4-diaminophenoxy)propane;
4,5-diamino-1-(2-hydroxyethyl)pyrazole 1-methoxy-2-amino-4-(2-hydroxyethylamino)benzene;
4,5-diamino-1-(2-hydroxyethyl)pyrazole/2-amino-3-hydroxypyridine;
4,5-diamino-1-(2-hydroxyethyl)pyrazole/1-naphthol.

9. The method according to claim 1, wherein the at least one oxidation dye precursor of the developer type applied in step b) is 4,5-diamino-1-(2-hydroxyethyl)pyrazole.

10. The method according to claim 1, wherein the time span between method steps a) and b) is from about 30 seconds to about 20 minutes.

11. The method according to claim 1, wherein the coloring agent applied in step b) is rinsed out of the fibers after a time of from about 5 to about 60 minutes.

* * * * *